(12) United States Patent
Wang et al.

(10) Patent No.: US 11,514,091 B2
(45) Date of Patent: Nov. 29, 2022

(54) EXTRACTING ENTITY RELATIONS FROM SEMI-STRUCTURED INFORMATION

(71) Applicant: INTERNATIONAL BUSINESS MACHINES CORPORATION, Armonk, NY (US)

(72) Inventors: Ke Wang, Beijing (CN); Pei Ni Liu, Beijing (CN); Wen Sun, Beijing (CN); Jing Min Xu, Beijing (CN); Songfang Huang, Beijing (CN); Yong Qin, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 998 days.

(21) Appl. No.: 16/241,000

(22) Filed: Jan. 7, 2019

(65) Prior Publication Data
US 2020/0218744 A1 Jul. 9, 2020

(51) Int. Cl.
*G16H 20/00* (2018.01)
*G16H 50/20* (2018.01)
(Continued)

(52) U.S. Cl.
CPC ......... *G06F 16/313* (2019.01); *G06K 9/6228* (2013.01); *G06N 3/04* (2013.01); *G16H 20/00* (2018.01); *G16H 50/20* (2018.01)

(58) Field of Classification Search
CPC .............................................. G06Q 50/20–26
See application file for complete search history.

(56) References Cited

U.S. PATENT DOCUMENTS

2014/0257805 A1* 9/2014 Huang .................. G06N 3/084
    704/232
2018/0203851 A1* 7/2018 Wu .......................... G06F 16/50
(Continued)

FOREIGN PATENT DOCUMENTS

CN          106202044       12/2016
CN          106446526       2/2017
(Continued)

OTHER PUBLICATIONS

Atienza, Rowel, "LSTM by Example using Tensorflow" as downloaded from https://towardsdatascience.com/lstm-by-example-using-tensorflow-feb0c1968537 (Year: 2017).*
(Continued)

*Primary Examiner* — Neal Sereboff
(74) *Attorney, Agent, or Firm* — Tutunjian & Bitetto, P.C.; Joseph Petrokaitis

(57) ABSTRACT

Methods and systems for processing records include extracting feature vectors from words in an unstructured portion of a record. The feature vectors are weighted based similarity to a topic vector from a structured portion of the record associated with the unstructured portion. The weighted feature vectors are classified using a machine learning model to determine respective probability vectors that assign a probability to each of a set of possible relations for each feature vector. Relations between entities are determined within the record based on the probability vectors. An action is performed responsive to the determined relations.

20 Claims, 8 Drawing Sheets

(51) Int. Cl.
*G06F 16/31* (2019.01)
*G06N 3/04* (2006.01)
*G06K 9/62* (2022.01)

(56) References Cited

U.S. PATENT DOCUMENTS

| | | | | |
|---|---|---|---|---|
| 2020/0034436 | A1* | 1/2020 | Chen | G06N 3/0454 |
| 2020/0065374 | A1* | 2/2020 | Gao | G06F 40/295 |
| 2020/0097820 | A1* | 3/2020 | Song | G06N 3/0454 |
| 2022/0014807 | A1* | 1/2022 | Lin | G06N 3/0445 |

FOREIGN PATENT DOCUMENTS

| | | |
|---|---|---|
| CN | 106776711 | 5/2017 |
| CN | 107609163 | 1/2018 |

OTHER PUBLICATIONS

Define "administer" Google (Year: 2022).*
Brownless, Jason, "A Gentle Introduction to the Bag-of-Words Model" as downloaded from https://machinelearningmastery.com/gentle-introduction-bag-words-model/ (Year: 2019).*
Sharma, Vinod, "How Neural Network Algorithms Works : An Overview" as downloaded from https://vinodsblog.com/2018/12/31/how-neural-network-algorithms-works-an-overview/ (Year: 2018).*
J. Betina Antony et al., Entity Relation Extraction for Indigenous Medical Text, Smart Innovations in Communication and Computational Sciences, Jun. 2018, pp. 153-162.
Zhao Liu et al., A Semi-automated Entity Relation Extraction Mechanism with Weakly Supervised Learning for Chinese Medical Webpages, International Conference on Smart Health, May 2017.
Fei Li et al., A neural joint model for entity and relation extraction from biomedical text, BMC Bioinformatics, Mar. 2017.
Yi Yao Huang et al., Deep Residual Learning for Weakly-Supervised Relation Extraction, Computation and Language, Jul. 2017.

* cited by examiner

EXTRACTING ENTITY RELATIONS FROM SEMI-STRUCTURED INFORMATION

BACKGROUND

Technical Field

The present invention generally relates to natural language processing and, more particularly, to the identification of entity relations using structured and unstructured information.

Description of the Related Art

Existing natural language processing technologies have difficulty extracting entity relations from documents with precision. Many existing approaches are only able to recognize relations within a single sentence, thereby losing important contextual information from other portions of a document.

SUMMARY

A method for processing records includes processing records include extracting feature vectors from words in an unstructured portion of a record. The feature vectors are weighted based similarity to a topic vector from a structured portion of the record associated with the unstructured portion. The weighted feature vectors are classified using a machine learning model to determine respective probability vectors that assign a probability to each of a set of possible relations for each feature vector. Relations between entities are determined within the record based on the probability vectors. An action is performed responsive to the determined relations A record processing system includes a feature module configured to extract feature vectors from words in an unstructured portion of a record. A weighting module is configured to weight the feature vectors based similarity to a topic vector from a structured portion of the record associated with the unstructured portion. A machine learning model is implemented using a processor configured to classify the weighted feature vectors to determine respective probability vectors that assign a probability to each of a set of possible relations for each feature vector. A relation module is configured to determine relations between entities within the record based on the probability vectors. A treatment control module is configured to perform an action responsive to the determined relations.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Figure 1:
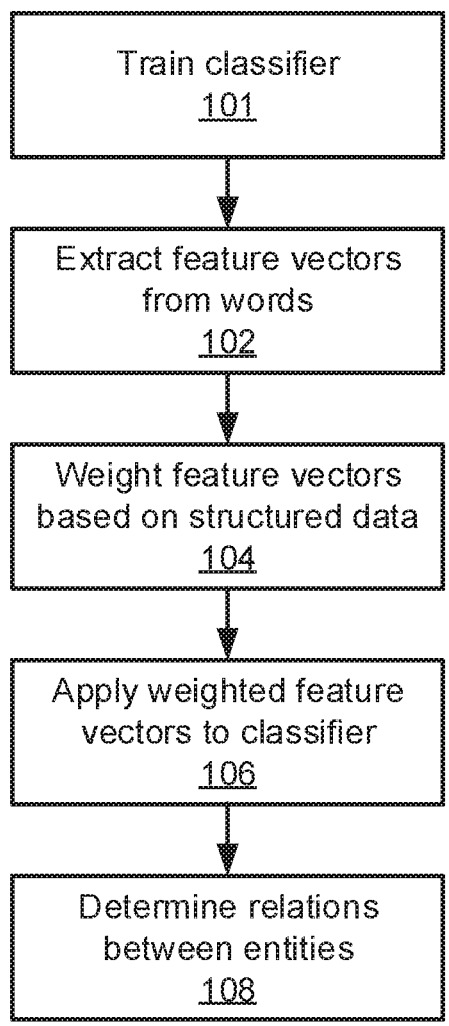
FIG. 1 is a block/flow diagram of a method of extracting entities and relations from semi-structured textual records in accordance with an embodiment of the present invention.

Embodiments of the present invention identify entities within a document and extract relations between such entities using both structured and unstructured information. The structured information is used to determine the relevance of words in a sentence of unstructured text, providing a weighting value to each word. A set of features for each word is extracted from the text and are used with a neural network model to identify relations within the document.

In general, an "entity" or a "named entity" is an object that can be identified in text with a specific designation. For example, a specific person or place would be a named entity, as they can be identified with a proper name. Entities can also include specific, though not named, entities that include, for example, general objects or concepts. Thus, dates and times can be identified as entities. Entity identification in unstructured text can locate entities with near-human levels of reliability.

In one particular example, where semi-structured medical documents are used as input, entities can include such items as symptoms, tests, treatments, clinical departments, evidentials (words or phrases that indicate the source of information, such as the word, "complained"), and occurrences (other events such as, "admit," "transfer," or, "discharge" that affect a patient's timeline). In other embodiments, the entities can be determined automatically or can be determined according to any appropriate list.

However, automatically identifying the relationships between different entities, particularly within a document that is longer than a sentence, can be more challenging. For example, in the sentence, "Daphne got to the office before 9:00," the identified entities could be, "Daphne," "the office," and, "9:00." The relations between the entities in this exemplary sentence could include spatial relations (e.g., Daphne was "in" the office), temporal relations (e.g., Daphne was "before" 9:00), and any other appropriate relations. An illustrative list of relations includes: before, after, simultaneous, overlap, begun_by, ended_by, during, and before_overlap.

While this is straightforward when the relation is indicated within a relatively short distance of the entity (e.g., within a single sentence), entity extraction is significantly more challenging when looking to the larger document. In one particular example, medical records may include structured and unstructured data that all bear on the relations it describes. For example, the medical record may have a time and date of admission. It can be inferred that any circumstances described in the unstructured data relating to the patient's condition will have occurred before the date of admission. The present embodiments make use of the information included in structured data to weight feature vectors of the unstructured data before providing those feature vectors to a neural network for classification. It should be understood that, although neural networks are specifically addressed herein as one potential machine learning model that can be used for classification, any other appropriate machine learning model can be used instead.

Referring now to the drawings in which like numerals represent the same or similar elements and initially to FIG. 1, a method for extracting the relations between entities in semi-structured text is shown. Block 101 begins by training a neural network classifier using an appropriate corpus of training data. The training data can include documents that have one or more sections of structured data, each corresponding to one or more sections of unstructured data. The training data is annotated to identify entities and relations in the data. During training, a first portion of the training data is used to train the neural network. A second portion of the training data is then used to verify that the neural network is producing correct outputs, with the outputs generated by the neural network for the second portion of the training data being compared to the expected values to generate error information.

Block 102 extracts feature vectors from words in an input document. It is specifically contemplated that each word in a section of unstructured data will have an associated feature vector. Any appropriate features of the words can be used to form the feature vector, but it is specifically contemplated that each feature vector can include such features as the word itself, the word's part of speech, the word's position in the document, and an entity type. The entity type defines a collection or set of entities that have similar attributes. Exemplary entity types in the context of medical documents include "test," "symptom," "treatment," etc.

Vector representations of the words can be used using tools such as word2vec, which map a word to a multi-dimensional semantic space, where similarity between vectors in the semantic space represents a similarity in meaning for the corresponding words. Thus the "word" feature of the feature vectors is itself represented as a vector in the semantic space. Similarity between words can be determined by any appropriate mechanism including, for example, a cosine similarity.

The unstructured data in the input document can be in any format. It is specifically contemplated that the unstructured data may include text data, but it should be understood that other types of unstructured data may be included such as, e.g., audio or visual data. The structured data can similarly be in any format, though annotated text is specifically contemplated. The annotated text can include, for example, a set of words and a designation of what the words represent. In one example, the structured data can include a section heading, with the text representing a topic for the associated unstructured data. In another example, the structured data can include a data and time, representing a time at which the unstructured data was recorded or a time at which an event described in the unstructured data took place.

Block 104 weights the feature vectors in accordance with the structured data. The structured data is treated as a topic for the section, and a relevance score is calculated for each word in the unstructured data relative to the topic. As noted above, the similarity between two vectors in the semantic space can be determined using any appropriate similarity metric, such as the cosine similarity. The topic from the structured data is converted to a vector representation and the similarity between it and each word in the unstructured data is determined.

Block 106 applies the weighted feature vectors as input to a classifier. The input can be formed as an m×n matrix that is made up of the feature vectors of all the sentences in the unstructured data, where m is the maximum length of all the sentences and n is the dimension of a feature vector. Any sentences below the maximum length can be padded by a special word to ensure that all the sentences' respective concatenated feature vectors are equal length. It should be understood that any appropriate classifier can be used, but it is specifically contemplated that the classifier can be implemented as a neural network. The structure of the neural network is described in greater detail below. All of the feature vectors for all of the words in the unstructured data are concatenated into a single input feature vector. The output of the classifier can be a probability vector that includes probabilities for all possible relation types between two entities.

The dimension of the output probability vector is equal to the number of possible relations between entities. For example, an output vector of [0.8, 0.2, 0.4, 0.2, 0.5, 0.2, 0.4, 0.2] would predict that the relation is most likely the first relation in the list represented by the different values of the vector.

Block 108 determines relations between the entities based on the probability vector output by the classifier. Block 108 compares each value of the probability vector to a threshold, with probability values that are above the threshold representing potential relations. If there are multiple relations having a probability value above the threshold, then block 108 can select the relation having the highest probability value. If no relation has a probability value above the threshold, then no relation is indicated for the pair of entities.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

An artificial neural network (ANN) is an information processing system that is inspired by biological nervous systems, such as the brain. The key element of ANNs is the structure of the information processing system, which includes a large number of highly interconnected processing elements (called "neurons") working in parallel to solve specific problems. ANNs are furthermore trained in-use, with learning that involves adjustments to weights that exist between the neurons. An ANN is configured for a specific application, such as pattern recognition or data classification, through such a learning process.

Figure 2:
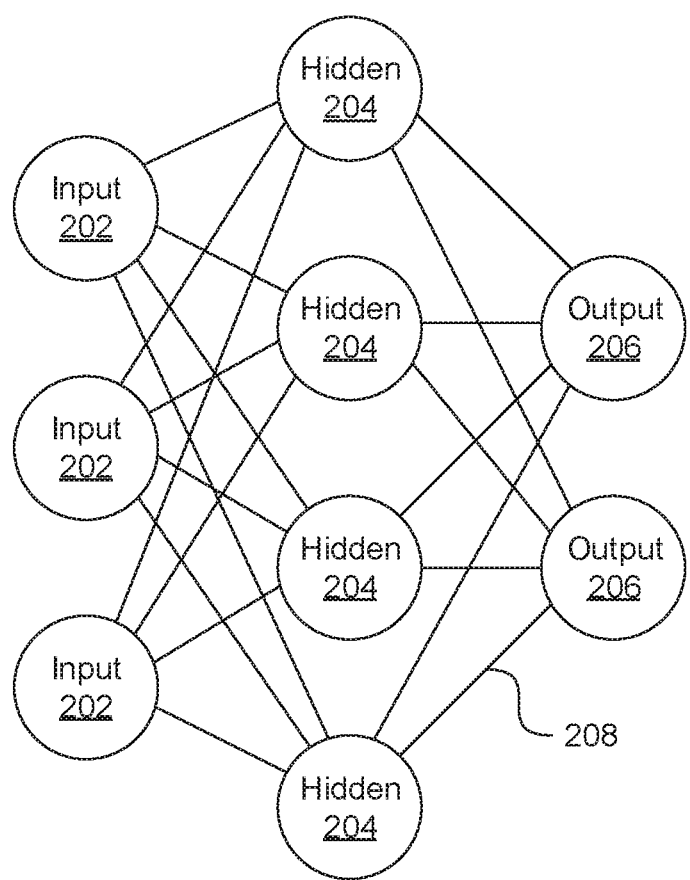
FIG. 2 is a diagram of an exemplary artificial neural network in accordance with an embodiment of the present invention.

Referring now to FIG. 2, a generalized diagram of a neural network is shown. ANNs demonstrate an ability to derive meaning from complicated or imprecise data and can be used to extract patterns and detect trends that are too complex to be detected by humans or other computer-based systems. The structure of a neural network is known generally to have input neurons 202 that provide information to one or more "hidden" neurons 204. Connections 208 between the input neurons 202 and hidden neurons 204 are weighted and these weighted inputs are then processed by the hidden neurons 204 according to some function in the hidden neurons 204, with weighted connections 208 between the layers. There may be any number of layers of hidden neurons 204, and as well as neurons that perform different functions. There exist different neural network structures as well, such as convolutional neural network, maxout network, etc. Finally, a set of output neurons 206 accepts and processes weighted input from the last set of hidden neurons 204.

This represents a "feed-forward" computation, where information propagates from input neurons 202 to the output neurons 206. Upon completion of a feed-forward computation, the output is compared to a desired output available from training data. The error relative to the training data is then processed in "feed-back" computation, where the hidden neurons 204 and input neurons 202 receive information regarding the error propagating backward from the output neurons 206. Once the backward error propagation has been completed, weight updates are performed, with the weighted connections 208 being updated to account for the received error. This represents just one variety of ANN.

Figure 3:
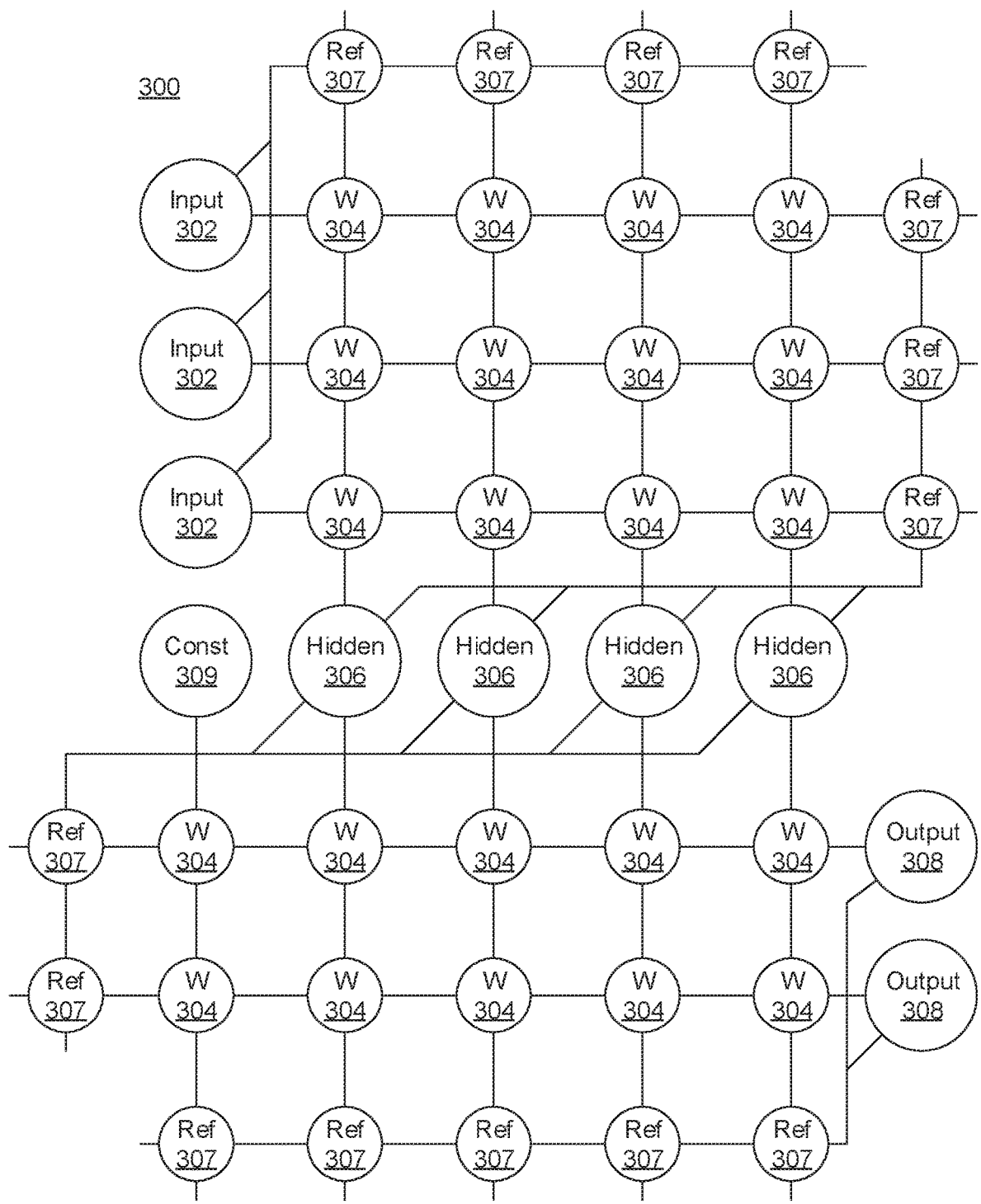
FIG. 3 is a diagram of a detailed structure for an exemplary neural network in accordance with an embodiment of the present invention.

Referring now to the drawings in which like numerals represent the same or similar elements and initially to FIG. 3, an artificial neural network (ANN) architecture 300 is shown. It should be understood that the present architecture is purely exemplary and that other architectures or types of neural network may be used instead. In particular, while a hardware embodiment of an ANN is described herein, it should be understood that neural network architectures can be implemented or simulated in software. The hardware embodiment described herein is included with the intent of illustrating general principles of neural network computation at a high level of generality and should not be construed as limiting in any way.

Furthermore, the layers of neurons described below and the weights connecting them are described in a general manner and can be replaced by any type of neural network layers with any appropriate degree or type of interconnectivity. For example, layers can include convolutional layers, pooling layers, fully connected layers, softmax layers, or any other appropriate type of neural network layer. Furthermore, layers can be added or removed as needed and the weights can be omitted for more complicated forms of interconnection.

During feed-forward operation, a set of input neurons 302 each provide an input voltage in parallel to a respective row of weights 304. In the hardware embodiment described herein, the weights 304 each have a settable resistance value, such that a current output flows from the weight 304 to a respective hidden neuron 306 to represent the weighted input. In software embodiments, the weights 304 may simply be represented as coefficient values that are multiplied against the relevant neuron outputs.

Following the hardware embodiment, the current output by a given weight 304 is determined as $$I = \frac{V}{r},$$

where V is the input voltage from the input neuron 302 and r is the set resistance of the weight 304. The current from each weight adds column-wise and flows to a hidden neuron 306. A set of reference weights 307 have a fixed resistance and combine their outputs into a reference current that is provided to each of the hidden neurons 306. Because conductance values can only be positive numbers, some reference conductance is needed to encode both positive and negative values in the matrix. The currents produced by the weights 304 are continuously valued and positive, and therefore the reference weights 307 are used to provide a reference current, above which currents are considered to have positive values and below which currents are considered to have negative values. The use of reference weights 307 is not needed in software embodiments, where the values of outputs and weights can be precisely and directly obtained. As an alternative to using the reference weights 307, another embodiment may use separate arrays of weights 304 to capture negative values.

The hidden neurons 306 use the currents from the array of weights 304 and the reference weights 307 to perform some calculation. The hidden neurons 306 then output a voltage of their own to another array of weights 304. This array performs in the same way, with a column of weights 304 receiving a voltage from their respective hidden neuron 306 to produce a weighted current output that adds row-wise and is provided to the output neuron 308.

It should be understood that any number of these stages may be implemented, by interposing additional layers of arrays and hidden neurons 306. It should also be noted that some neurons may be constant neurons 309, which provide a constant output to the array. The constant neurons 309 can be present among the input neurons 302 and/or hidden neurons 306 and are only used during feed-forward operation.

During back propagation, the output neurons 308 provide a voltage back across the array of weights 304. The output layer compares the generated network response to training data and computes an error. The error is applied to the array as a voltage pulse, where the height and/or duration of the pulse is modulated proportional to the error value. In this example, a row of weights 304 receives a voltage from a respective output neuron 308 in parallel and converts that voltage into a current which adds column-wise to provide an input to hidden neurons 306. The hidden neurons 306 combine the weighted feedback signal with a derivative of its feed-forward calculation and stores an error value before outputting a feedback signal voltage to its respective column of weights 304. This back propagation travels through the entire network 300 until all hidden neurons 306 and the input neurons 302 have stored an error value.

During weight updates, the input neurons 302 and hidden neurons 306 apply a first weight update voltage forward and the output neurons 308 and hidden neurons 306 apply a second weight update voltage backward through the network 300. The combinations of these voltages create a state change within each weight 304, causing the weight 304 to take on a new resistance value. In this manner the weights 304 can be trained to adapt the neural network 300 to errors in its processing. It should be noted that the three modes of operation, feed forward, back propagation, and weight update, do not overlap with one another.

As noted above, the weights 304 can be implemented in software or in hardware, for example using relatively complicated weighting circuitry or using resistive cross point devices. Such resistive devices may have switching characteristics that have a non-linearity that can be used for processing data. The weights 304 may belong to a class of device called a resistive processing unit (RPU), because their non-linear characteristics are used to perform calculations in the neural network 300. The RPU devices may be implemented with resistive random access memory (RRAM), phase change memory (PCM), programmable metallization cell (PMC) memory, or any other device that has non-linear resistive switching characteristics. Such RPU devices may also be considered as memristive systems.

Figure 4:
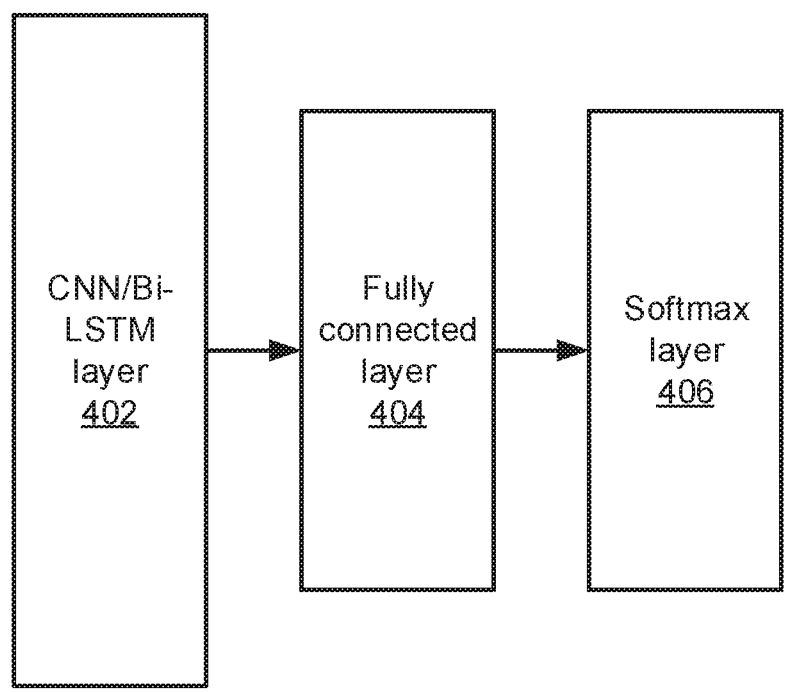
FIG. 4 is a diagram of a machine learning classifier for extracting entities from semi-structured textual records implemented as an artificial neural network in accordance with an embodiment of the present invention.

Referring now to FIG. 4, a diagram of an exemplary neural network that is configured to classify feature vectors is shown. A first layer 402 can be implemented as a convolutional neural network (CNN) layer or as a bidirectional long-short term memory (LSTM) layer. Global features from the input feature vector can be obtained by a bi-directional LSTM layer, in which global information is obtained by progressive recursion. Local features from the input features vector can be obtained by a CNN layer, in which local information can be obtained by a convolution kernel with limited size. In some embodiments, both types of layer may be used. This layer obtains local and global features from the input feature vector. The input to the first layer 402 can take a complete sentence from the unstructured data, weighted by the structured data as described above. A fully connected feed-forward layer 404 is then used to make the classifier over the features. A softmax layer 406 generates the probability vector output using the output of the fully collected feed-forward layer 404.

Figure 5:
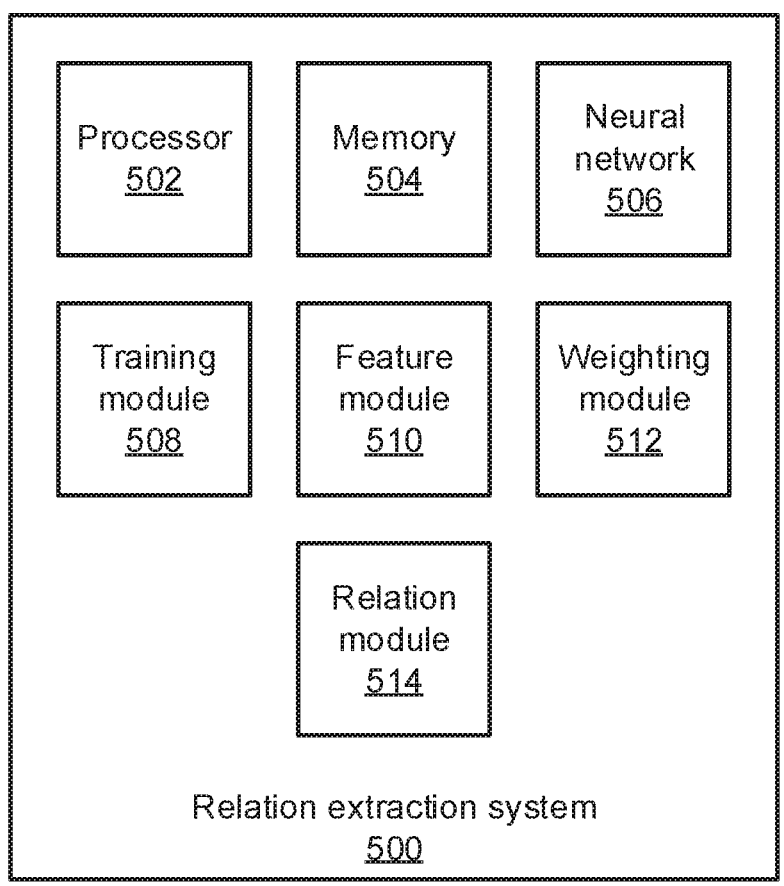
FIG. 5 is a block diagram of a relation extraction system that extracts entities and relations from semi-structured textual records in accordance with an embodiment of the present invention.

Referring now to FIG. 5, a relation extraction system 500 is shown. The system 500 includes a hardware processor 502 and memory 504. A neural network 506 is implemented at the system 500 as either software or as a dedicated hardware network. The system 500 furthermore includes one or more functional modules that may, in some embodiments, be implemented in software that is stored in the memory 504 and that is executed by hardware processor 502. In other embodiments, one or more of the functional modules can be implemented as one or more discrete hardware components in the form of, e.g., application specific integrated chips or field programmable gate arrays.

A training module 508 trains the neural network 506 using a corpus of training data. A feature module 506 accepts input data that includes both structured data and unstructured data and identifies features within the unstructured data as described above to determine feature vectors for each word in the unstructured data. A weighting module 512 captures the structured data and uses a similarity metric to determine the relevance of each word in the unstructured data to a topic defined by the structured data. The weighting module thereby determines weights for each of the feature vectors.

The neural network 506 accepts the weighted feature vectors as an input and outputs a probability vector that captures the relations between entities in the unstructured data. A relation module 514 then uses the probability vector to determine what these relations are.

Figure 6:
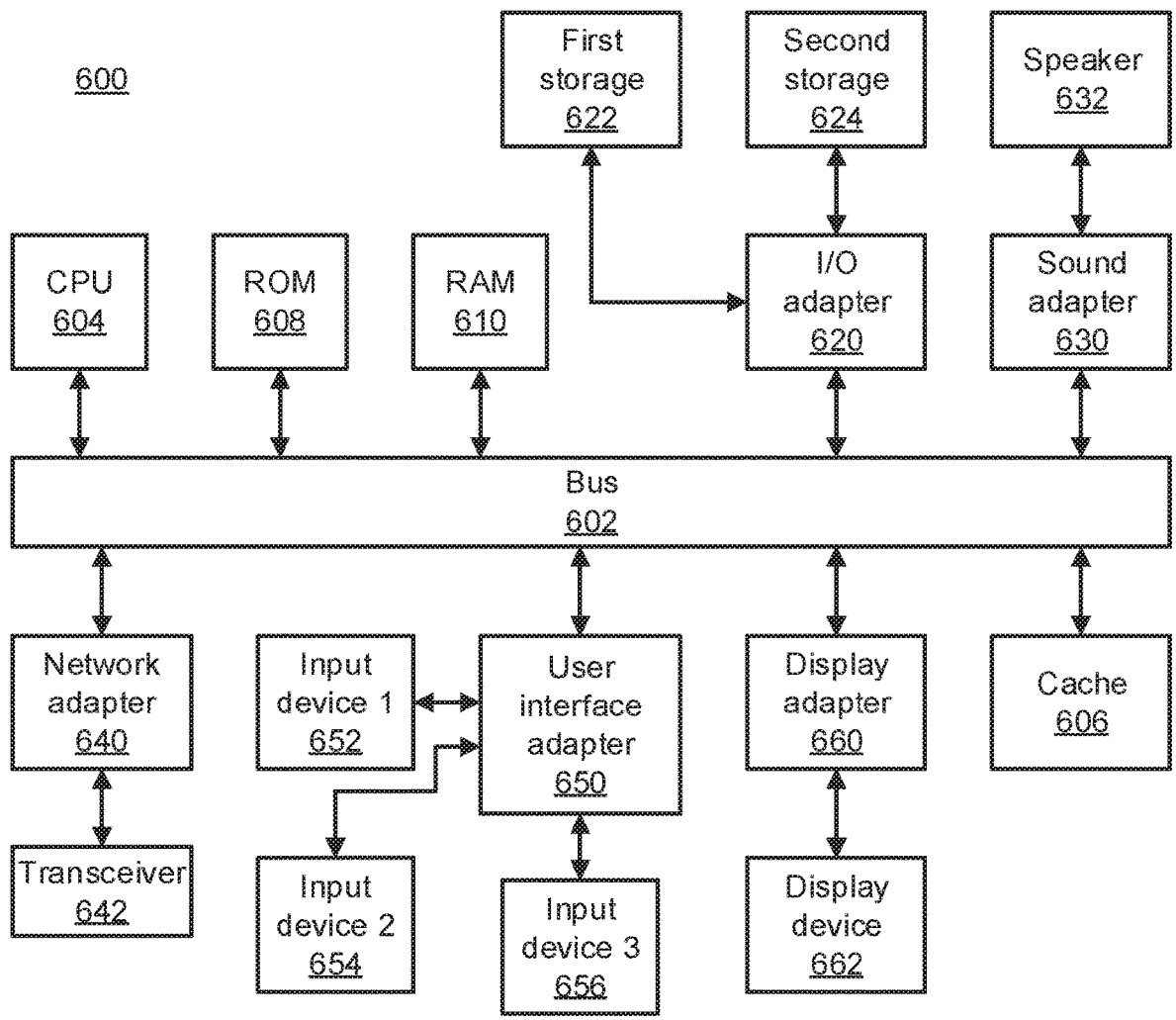
FIG. 6 is a block diagram of a processing system in accordance with an embodiment of the present invention.

Referring now to FIG. 6, an exemplary processing system 600 is shown which may represent the relation extraction system 500. The processing system 600 includes at least one processor (CPU) 604 operatively coupled to other components via a system bus 602. A cache 606, a Read Only Memory (ROM) 608, a Random Access Memory (RAM) 610, an input/output (I/O) adapter 620, a sound adapter 630, a network adapter 640, a user interface adapter 650, and a display adapter 660, are operatively coupled to the system bus 602.

A first storage device 622 and a second storage device 624 are operatively coupled to system bus 602 by the I/O adapter 620. The storage devices 622 and 624 can be any of a disk storage device (e.g., a magnetic or optical disk storage device), a solid state magnetic device, and so forth. The storage devices 622 and 624 can be the same type of storage device or different types of storage devices.

A speaker 632 is operatively coupled to system bus 602 by the sound adapter 630. A transceiver 642 is operatively coupled to system bus 602 by network adapter 640. A display device 662 is operatively coupled to system bus 602 by display adapter 660.

A first user input device 652, a second user input device 654, and a third user input device 656 are operatively coupled to system bus 602 by user interface adapter 650. The user input devices 652, 654, and 656 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 652, 654, and 656 can be the same type of user input device or different types of user input devices. The user input devices 652, 654, and 656 are used to input and output information to and from system 600.

Of course, the processing system 600 may also include other elements (not shown), as readily contemplated by one of skill in the art, as well as omit certain elements. For example, various other input devices and/or output devices can be included in processing system 600, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 600 are readily contemplated by one of ordinary skill in the art given the teachings of the present principles provided herein.

It should be understood that the present embodiments are applicable in a wide variety of different contexts. In the example of the medical fields, the automatic extraction of entities and their relations makes it possible to enact automatic medical decision making. In such an example, an automated system can make a diagnosis based on existing medical records, with particular relations between entities representing symptoms, speed of onset, and other disease characteristics. In one specific example, a system that is configured to automatically administer treatment to a user by, e.g., providing therapeutic pharmaceuticals in response to a patient's condition, can automatically assess the medical records for the patient and any new observations made by attending medical professionals and can alter or administer treatments in response to extracted relations. The automated system can make such decisions based on a knowledge base that associates particular relations with specific user conditions and treatments. Thus, in a situation where the knowledge base indicates that a particular treatment is needed and has a low risk, the system can automatically administer the treatment after obtaining the informed consent of the patient.

Figure 7:
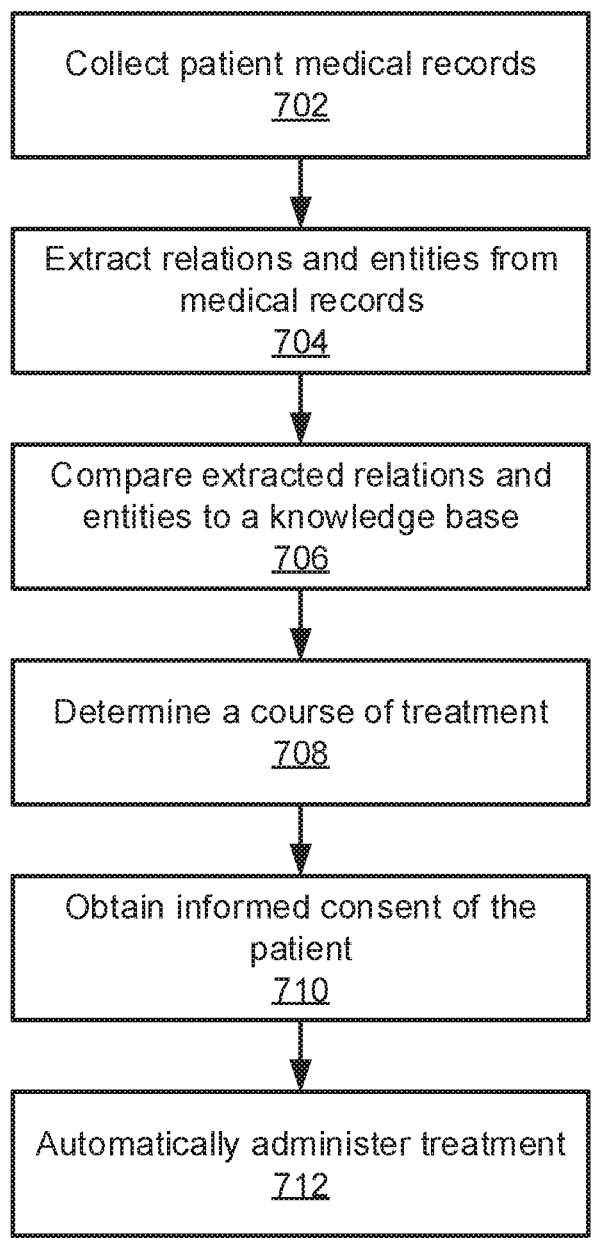
FIG. 7 is a block/flow diagram of a method for automatically performing medical treatments based on information extracted from semi-structured medical records in accordance with an embodiment of the present invention.

Referring now to FIG. 7, a method for automatically treating a patient is shown. Block 702 collects semi-structured medical records regarding the patient. The semi-structured medical records include at least one structured field that is associated with at least one unstructured field, where the structured field includes topic information relating to information stored in the unstructured field. Block 704 extracts entities and relations from the semi-structured medical records, for example in the manner described above.

Block 706 compares the extracted relations and entities to a knowledge base that associates such information with particular treatments for a user. Block 708 uses the information from the knowledge base to determine a course of treatment. Block 710 obtains the informed consent of the patient and block 712 then automatically administers the treatment to the user. In this manner, treatment can be rapidly determined and administered without the direct intervention of a medical professional, based solely on the patient's medical records. In addition, a patient's entire medical history can be assessed at once, greatly speeding diagnostic efforts.

Figure 8:
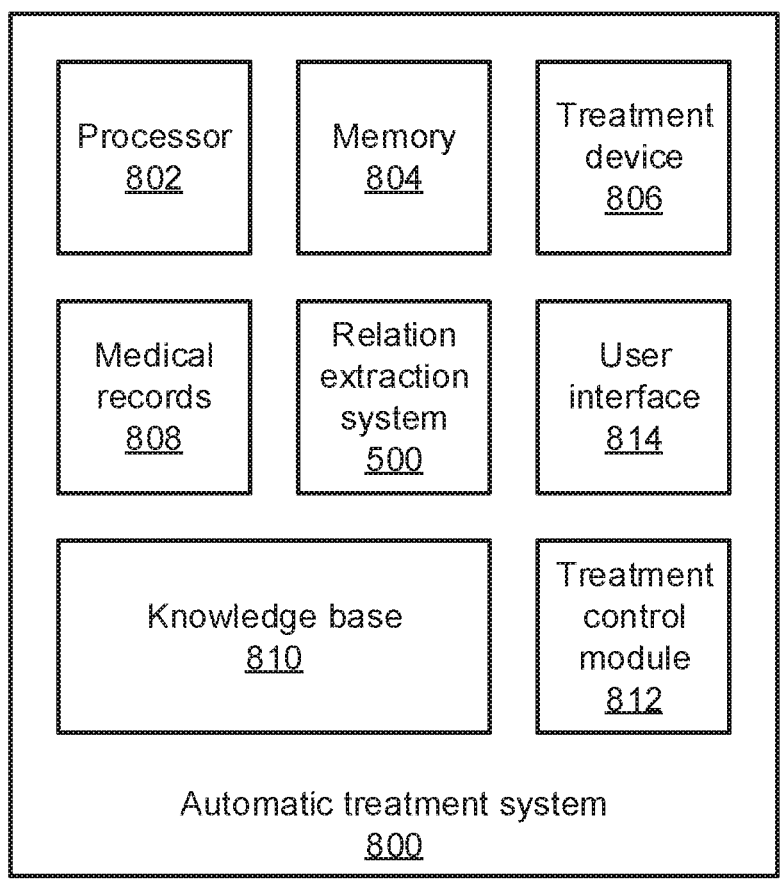
FIG. 8 is a block diagram of a system for automatically performing medical treatments based on information extracted from semi-structured medical records in accordance with an embodiment of the present invention.

Referring now to FIG. 8, an automatic treatment system 800 is shown. The treatment system 800 includes a hardware processor 802 and a memory 804. A treatment device 806 interacts with a patient, for example in the form of an intravenous line to administer pharmaceuticals. It should be understood that the treatment device 806 can represent any appropriate medical device that can be automatically activated. The automatic treatment system 800 further includes a user interface 814 that can provide information to a patient and receive inputs from the patient. The system 800 further includes one or more functional modules that can be implemented in the same manner as the functional modules described above with respect to FIG. 5.

A set of medical records 808 for the patient are stored in the memory 804. These medical records can be input by a medical professional and can further include biometrics measured directly by the system 800. A relation extraction system 500 extracts entities and relations from the medical records 808. It should be understood that the hardware processor 502 described above with respect to the relation extraction system 500 can be the same as hardware processor 802 or may represent a distinct physical component. A treatment control module 812 uses the extracted entities and relations to refer to a knowledge base 810 and determine a course of treatment. The treatment control module 812 obtains the patient's informed consent using the user interface 814 before automatically instructing the treatment device 806 to proceed with the determined treatment.

Having described preferred embodiments of extracting entity relations from semi-structured information (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for processing records, comprising:
   obtaining a record having a structured portion and an unstructured portion, wherein the record contains a plurality of entities;
   extracting feature vectors from words in an unstructured portion of the record;
   weighting the feature vectors based on a similarity to a topic vector that is derived from a structured portion of the record;
   classifying the weighted feature vectors using a neural network model to determine respective probability vectors, wherein each probability vector includes a probability for each of a set of possible relations;
   determining relations between entities within the record based on the probability vectors; and
   performing an action responsive to the determined relations.

2. The computer-implemented method of claim 1, wherein the neural network model includes a first layer selected from the group consisting of a convolutional neural network layer and a bi-directional long-short term memory layer.

3. The computer-implemented method of claim 2, wherein the neural network model further comprises a fully connected layer that accepts the output of the first layer and a softmax layer that accepts an output of the fully connected layer.

4. The computer-implemented method of claim 1, wherein extracting the feature vectors comprises embedding each word in the unstructured portion in a semantic space.

5. The computer-implemented method of claim 4, further comprising embedding words from the structured portion in the semantic space to form the topic vector.

6. The computer-implemented method of claim 5, wherein weighting the feature vectors comprises determining the similarity as a cosine similarity within the semantic space.

7. The computer-implemented method of claim 1, wherein determining relations comprises determining that a highest-probability relation represents a pair of entities.

8. The computer-implemented method of claim 1, wherein the records are medical records and the unstructured portion comprises information relating to a patient's medical condition.

9. The computer-implemented method of claim 8, wherein performing the action comprises automatically administering a treatment to the patient based on the determined relations.

10. The computer-implemented method of claim 9, further comprising comparing the determined relations to a medical knowledge base to determine the treatment.

11. A non-transitory computer readable storage medium comprising a computer readable program for processing records, wherein the computer readable program when executed on a computer causes the computer to perform the steps of:
    obtaining a record having a structured portion and an unstructured portion, wherein the record contains a plurality of entities;
    extracting feature vectors from words in an unstructured portion of the record;
    weighting the feature vectors based on a similarity to a topic vector that is derived from a structured portion of the record;
    classifying the weighted feature vectors using a neural network model to determine respective probability vectors, wherein each probability vector includes a probability for each of a set of possible relations;

determining relations between entities within the record based on the probability vectors; and performing an action responsive to the determined relations.

12. A record processing system, comprising:
a feature module configured to obtain a record having a structured portion and an unstructured portion, wherein the record contains a plurality of entities, and to extract feature vectors from words in an unstructured portion of the record;
a weighting module configured to weight the feature vectors based on a similarity to a topic vector that is derived from a structured portion of the record;
a neural network model implemented using a processor configured to classify the weighted feature vectors to determine respective probability vectors, wherein each probability vector includes a probability for each of a set of possible relations;
a relation module configured to determine relations between entities within the record based on the probability vectors; and
a treatment control module configured to perform an action responsive to the determined relations.

13. The system of claim 12, wherein the neural network model includes a first layer selected from the group consisting of a convolutional neural network layer and a bi-directional long-short term memory layer.

14. The system of claim 13, wherein the neural network model further comprises a fully connected layer that accepts the output of the first layer and a softmax layer that accepts an output of the fully connected layer.

15. The system of claim 14, wherein the feature module is further configured to embed each word in the unstructured portion in a semantic space.

16. The system of claim 15, wherein the feature module is further configured to embed words from the structured portion in the semantic space to form the topic vector.

17. The system of claim 12, wherein the relation module is further configured to determine that a highest-probability relation represents a pair of entities.

18. The system of claim 12, wherein the records are medical records and the unstructured portion comprises information relating to a patient's medical condition.

19. The system of claim 18, wherein the treatment control module is further configured to administering a treatment to the patient based on the determined relations using a treatment device.

20. The system of claim 19, wherein the treatment control module is further configured to compare the determined relations to a medical knowledge base to determine the treatment.

* * * * *